United States Patent [19]
Goodman et al.

[11] Patent Number: 6,162,417
[45] Date of Patent: Dec. 19, 2000

[54] PYRROLO ISOQUINOLINES

[75] Inventors: Mark M. Goodman, Atlanta, Ga.; Bing Z. Shi, Cincinnati, Ohio

[73] Assignee: Emory University, Atlanta, Ga.

[21] Appl. No.: 09/073,729

[22] Filed: May 7, 1998

Related U.S. Application Data

[60] Provisional application No. 60/045,828, May 7, 1997.

[51] Int. Cl.[7] .......................... A61K 51/00; A61M 36/14
[52] U.S. Cl. .................. 424/1.85; 424/1.11; 424/9.1; 424/1.65; 424/9.4; 546/152; 548/400; 534/770
[58] Field of Search .................. 424/1.11, 1.65, 424/1.81, 1.85, 1.89, 9.1, 9.4; 206/223, 569, 570; 540/1; 546/1, 152; 548/400; 534/700

[56] References Cited

PUBLICATIONS

Suehiro et al, Nucl. Med. Biol, 1996 23(4), pp. 407–412, "Radiosynthesis and Biodistribution of S–[78F]Fluoroethyl Analog of McN5652", May 1996.

*Primary Examiner*—Dameron Jones
*Attorney, Agent, or Firm*—Greenlee Winner and Sullivan PC

[57] ABSTRACT

Compounds of the formula:

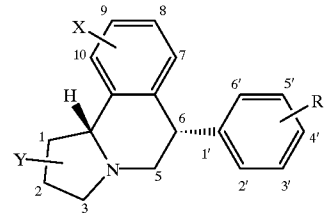

wherein X, Y, and R, independently of one another, is each a H; halogen, wherein said halogen is selected from the group consisting of $^{123}$I, $^{124}$I, $^{125}$I, $^{131}$I, $^{75}$Br, $^{76}$Br, $^{77}$Br, $^{82}$Br, $^{18}$F, or $^{210}$At; small alkyl, small alkenyl, or small alkynyl, any of which contains from one to about six carbon atoms and optionally having a carbon atom replaced by an O or S; or halogen substituted-small alkyl, halogen substituted-small alkenyl, or halogen substituted-small alkynyl wherein said compound contains at least one radioacitve halogen.

The compounds bind to the serotonin transporter. Depending upon the choice of halogen substituent, the compounds are useful for PET or SPECT imaging, diagnosis and treatment of psychiatric disorders such as depression, anxiety, obsessive-compulsive disorder, and other conditions associated with defects of serotonin transporter function.

35 Claims, 3 Drawing Sheets

PYRROLO ISOQUINOLINES

CROSS REFERENCE TO RELATED APPLICATIONS

This application claims priority to U.S. Provisional Application No. 60/045,828, filed May 7, 1997.

STATEMENT REGARDING FEDERALLY SPONSORED RESEARCH AND DEVELOPMENT

This invention was made, at least in part, with funding from the United States Department of Energy. Accordingly the United States Government has certain rights in this invention.

BACKGROUND OF THE INVENTION

The invention includes novel chemical compounds having specific binding in a biological system and capable of being used for positron emission tomography (PET) and single photon emission (SPECT) imaging methods.

The ability of analog compounds to bind to localized ligands within the body makes it possible to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, $[^{11}C]$, has been used for PET, but its short half-life of 20.5 minutes limits its usefulness to compounds that can be synthesized and purified quickly, and to facilities that are proximate to a cyclotron where the precursor $[^{11}C]$ starting material is generated. Other isotopes have even shorter half-lives. $[^{13}N]$ has a half-life of 10 minutes and $[^{15}O]$ has an even shorter half-life of 2 minutes. The emissions of both are more energetic than those of $[^{11}C]$. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope, $[^{18}F]$, has a half-life of 110 minutes. This allows sufficient time for incorporation into a radio-labeled tracer, for purification and for administration into a human or animal subject. In addition, facilities more remote from a cyclotron, up to about a 200 mile radius, can make use of $[^{18}F]$ labeled compounds. Disadvantages of $[^{18}F]$ are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}F$-F. Reactions using $^{18}F$-F as starting material therefore yield products having only one half the radionuclide abundance of reactions utilizing $K^{18}F$ as starting material. On the other hand, $[^{18}F]$ can be prepared in curie quantities as fluoride ion for incorporation into a radiopharmaceutical compound in high specific activity, theoretically 1.7 Ci/nmol using carrier-free nucleophilic substitution reactions. The energy emission of $[^{18}F]$ is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $[^{123}I]$, a γ-emitter with a 13.3 hour half life. Compounds labeled with $[^{123}I]$ can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of $[^{18}F]$ labeled compounds in PET has been limited to a few analog compounds. Most notably, $[^{18}F]$-fluorodeoxyglucose has been widely used in studies of glucose metabolism and localization of glucose uptake associated with brain activity. $[^{18}F]$-L-fluorodopa and other dopamine receptor analogs have also been used in mapping dopamine receptor distribution.

Other halogen isotopes can serve for PET or SPECT imaging, or for conventional tracer labeling. These include $^{75}Br$, $^{76}Br$, $^{77}Br$ and $^{82}Br$ which have usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs. Astatine can be substituted for other halogen isotopes; $[^{210}At]$ emits alpha particles with a half-life of 8.3 h. At-substituted compounds are therefore useful for tumor therapy, where binding is sufficiently tumor-specific.

Serotonin transporters are proteins that reside on the membrane of the nerve terminals of the presynaptic serotoninergic neurons. The serotonin transporter binds serotonin released during synaptic transmission by serotoninergic neurons, removing serotonin from the synapse. The serotonin transporter therefore serves to regulate the level of neurotransmitter in serotoninergic nerve transmission. Serotonin transporter is known to be involved in the pathophysiology of major depression and is the site of action of the majority of antidepressants, [See Murphy, D. L. et al. (1986) *J. Clin. Psychiatr.* 47:(suppl)9–15]. Supporting evidence for serotonin transporter function has been indirect, based on studies of post mortem tissue and of animal and peripheral cell models of transporter cell function and pharmacology. Direct evidence from emission tomography is needed to further define the functional status and pharmacology of serotonin transporter and antidepressant medication in the living human brain. A valuable tool for such studies would be the development of imaging agents labeled with positron emitters as probes to study the in vivo function of this neuroregulatory site by PET, or by SPECT using γ-emitting probes.

Currently, there does not exist a single radiopharmaceutical that can be labeled with either fluorine-18 and iodine-123 amenable for regional distribution that is efficacious in differentiating major depression from other psychiatric disorders. Citalopram [Hume et al. (1991) *Nucl. Med. Biol.* 18:339–351], paroxetine [Suehiro et al. (1991) *Nucl. Med. Biol.* 18:791–796], fluoxetine [Kilbourn et al. (1989) *J. Label. Cmpd. Radiopharm.* 26:412–414], and nitroquipazine [Mathis et al. (1993) *J. Nucl. Med.* 34:7P-8P], potent serotonin transporter ligands, have been radiolabeled with carbon-11 and fluorine-18 as potential radiotracers for localizing and quantifying serotonin transporter sites in the brain using PET. Unfortunately, the in vivo affinity and selectivity for the serotonin transporter of these radiolabeled ligands did not reflect their in vitro potencies as reflected in poor quality images of brain regions rich in serotoninergic neurons. Recently, a series of trans-1,2,3,5,6,10b-hexahydro-pyrrolo(2,1-a]isoquinoline derivatives, have been found to be potent inhibitors with low and subnanomolar affinity for the serotonin transporter [Maryanoff et al. (1987) *J. Med. Chem.* 30:1433–1454]. The most potent inhibitor of the series, trans-1,2,3,5,6,10b-hexahydro-6-[4-(methylthio) phenyl]pyrrolo[2,1-a]isoquinoline (McN-5652Z) (Ki=0.68 nM), has been labeled with carbon-11 for use as a PET radioligand for mapping serotonin transporter sites [Suehiro et al. (1992) *J. Label Cmpd. Radiopharm.* 31:841–848]. Carbon-11 McN-5652Z showed the greatest accumulation in brain regions rich in serotoninergic neurons with greater cortex to cerebellum ratios (4.3 to 1) than previously tested PET serotonin transporter ligands [Suehiro et al. (1993) *J. Nucl. Med.* 34:120–127. However, the very short 20 minute half-life of carbon-11 is not ideal for longitudinal selective regional uptake of the radioligand and the presence of radiolabeled metabolites that is crucial in binding site imaging and tracer kinetic modeling. Thus, there exists a need for a probe with a longer half-life that demonstrates sub to low nanomolar affinity, high selectivity, and a low dissociation rate from the serotonin transporter binding site. Because the serotonin transporter plays a pivotal role in serotonin neurotransmission, the development of radiopharmaceuticals radiolabeled with gamma or positron emitting isotopes which exhibit pronounced brain uptake, very high selectivity and affinity for the transporter, and low nonspecific binding would be excellent for the measurement of the density of presynaptic serotonin transporter sites by emission tomography.

Various substituted pyrrolo isoquinolines have been described, including those with halo-substituents without, however, providing compounds that can be efficiently labeled with isotopic halogen to provide useful compounds for PET and/or SPECT imaging. Maryanoff, B. E. et al., U.S. Pat. No. 4,719,216 describes a variety of pyrrolo-isoquinolines, including some with a halogen substituent in the non-heterocyclic ring, a fluorine substituent on the heterocyclic ring and others with a perfluoro alkyl substituent on a phenyl group substituted at the 4-position. Synthesis required introduction of halogen at an early synthetic step. Related patents are U.S. Pat. Nos. 4,595,688 and 4,837,328. The latter describes a method of stereoselective synthesis at the 10b carbon. Maryanoff, B. E. et al., U.S. Pat. No. 4,908,450, describes certain salts of the same compounds and an alternative stereoselective reduction step during synthesis, European Patent 0 130 069 B1 is also related to the above U.S. patents. No utility for PET or SPECT imaging was disclosed.

Maryanoff, B. E., U.S. Pat. No. 4,713,386 has also described tetrahydroazeto [2,1-A] isoquinolines as compounds useful for treating depression. Halogen substituents can be present on the non-heterocyclic ring and also on a phenyl group substituted at the 4-position. No synthetic route allowing rapid substitution of an isotopic halogen as a late step of synthesis was described. No utility for PET or SPECT imaging was described.

Carson, J. R. et al., U.S. Pat. No. 4,572,911 described hexahydroindolinzine compounds having antidepressant properties. The compounds included those having a phenyl group at the 4 position which could have a halogen substituent. Halogen introduction was accomplished at an early step of the synthesis. No utility for PET or SPECT imaging was disclosed.

SUMMARY OF THE INVENTION

Provided are compounds of Formula I:

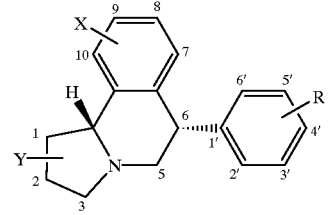

(I)

wherein X, Y and R, independently of one another, is each an H; halogen; small alkyl, small alkenyl, or small alkynyl; or halogen substituted-small alkyl, halogen substituted-small alkenyl, or halogen substituted-small alkynyl. The term "halogen" refers to radioactive and non-radioactive isotopes of fluorine, chlorine, bromine, iodine and astatine, and specifically includes Cl, I, $^{123}$I, $^{124}$I, $^{125}$I, $^{131}$I, Br, $^{75}$Br, $^{76}$Br, $^{77}$Br, $^{82}$Br, F, $^{18}$F, At, $^{211}$At and $^{210}$At. Small alkyl, small alkenyl, and small alkynyl have from one to about 6 carbon atoms, more preferably one to about 3 carbon atoms, and may have a carbon atom replaced by an O or S.

In particular are provided compounds wherein R is in the 4' position, X is in the 10 position, and/or Y is in the 2 or 3 position.

Specifically provided are compounds of the Formula II:

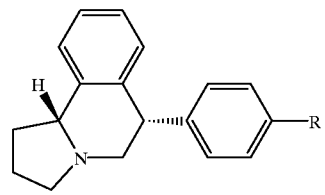

(II)

wherein R is selected from the group consisting of halogen; small alkyl, small alkenyl, or small alkynyl; or halogen substituted-small alkyl, halogen substituted-small alkenyl, or halogen substituted-small alkynyl. Formula II is an example of Formula I wherein X and Y are each H, and R is in the 4' position.

Methods of synthesis are described that permit last step substitution of the halogen radiolabel such that the final compound can be purified to high specific activity. As a result, the useable half-life of the isotope has been maximized.

Methods are provided for conducting positron emission tomography or single photon emission tomography imaging of a subject comprising:

1) administering to the subject an image-generating amount of a compound of Formula I which contains at least one radioactive halogen, e.g. $^{123}$I, $^{125}$I, $^{131}$I, $^{75}$Br, $^{76}$Br, $^{77}$Br, and $^{18}$F and 2) measuring the distribution within the subject of the compound by positron emission tomography or single photon emission tomography.

Figure 1A:
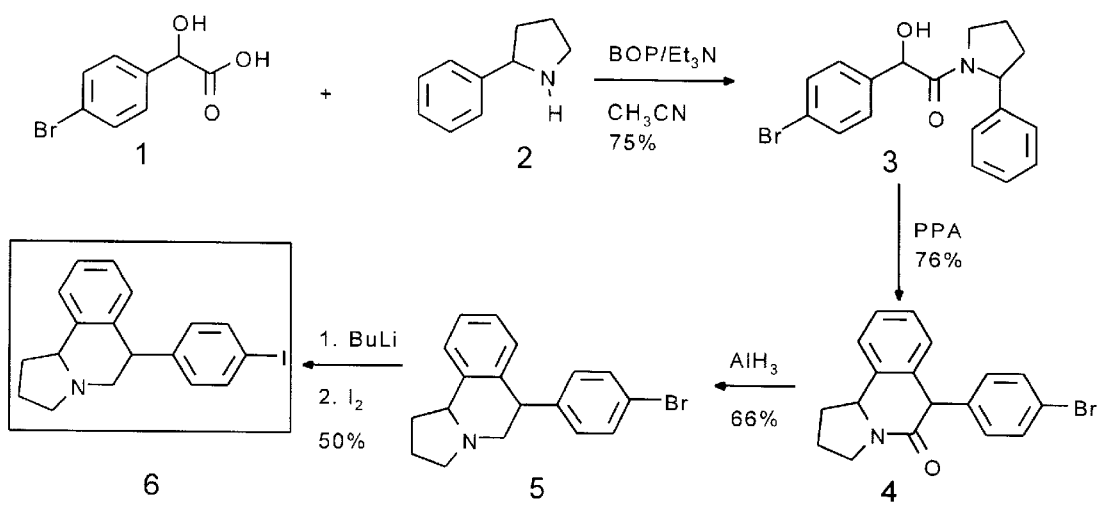
FIGS. 1A–1E provide exemplary synthetic routes for the compounds of this invention.

We have developed a new series of halopyrroloisoquinolines (HPI) of Formula I which can be substituted with:

1) halogens, including I, $^{123}$I, $^{124}$I, $^{125}$I, $^{131}$I, $^{75}$Br, $^{76}$Br, $^{77}$Br, $^{82}$Br, F, $^{18}$F, At, $^{210}$At and $^{211}$At;

2) small alkyl, small alkenyl, or small alkynyl, any of which contains from one to about 6 carbon atoms and may have a carbon atom replaced by an O or S; and/or halogen substituted-small alkyl, halogen substituted-small alkenyl, or halogen substituted-small alkynyl.

Preferred compounds for use in diagnosis and/or imaging, e.g. PET and SPECT, are compounds of Formula I containing at least one radioactive halogen isotope, either directly bonded to one of the rings of the pyrroloisoquinoline structure, or as the halogen substituent on a halogen substituted-small alkyl, halogen substituted-small alkenyl, or halogen substituted-small alkynyl. Preferred compounds for use in diagnosis and/or imaging, are compounds of Formula I containing a radioactive isotope with a half-life of about 2 hours or less.

Preferred compounds for use in treatment, e.g. for the treatment of psychiatric disorders such as depression, anxiety and obsessive-compulsive disorder, are those compounds of Formula I which do not contain a radioactive halogen isotope.

Preferred compounds for use in treatment of cancer (e.g. brain cancer, breast cancer, and leukemias) are compounds of Formula I containing a radioactive isotope with a half-life of about 6–10 hours or more, e.g. positron emitters with half-lives of about 6 hours or more, $^{210}$At, $^{211}$At and $^{131}$I.

Compounds containing a halogen which is a positron-emitting isotope, e.g. $^{76}$Br, $^{75}$Br and $^{18}$F, are useful for PET imaging of serotonin transporter distribution, for diagnosis of depression and other pathopsychological conditions affected by serotonin transporter function.

Compounds containing a halogen which is a γ-emitting halogen isotope, i.e. $^{75}$Br, $^{77}$Br, $^{82}$Br, $^{123}$I, $^{125}$I and $^{131}$I, are useful for SPECT localization and imaging of serotonin transporter and for diagnosis of depression and other pathopsychological conditions affected by serotonin transporter function.

Particularly preferred compounds include those with iodine-123 directly bonded to the pendant phenyl ring, i.e. R is $^{123}$I; and those with fluorine-18 bonded to the pyrrolo ring, i.e. Y is $^{18}$F; and those with a $^{18}$F-fluoroethyl or $^{18}$F-fluoroallyl bonded to the pendant phenyl ring. These groups are stable to metabolism and in vivo loss of the fluorine-18 and iodine-123 radioisotope. This allows labeling with either fluorine-18 or iodine-123 which gives rise to a radiopharmaceutical that can be used with either positron emission tomography (PET) or single photon emission (SPECT) imaging modalities.

Table 1 shows preferred compounds of this invention, compounds of Formula III, by listing preferred combinations of R, X and Y. Formula III is a preferred embodiment of Formula I; X, Y and R in Formula III are as defined for Formula I.

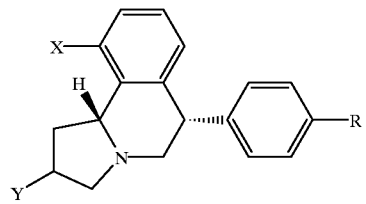

(III)

TABLE 1

Preferred Pyrrolo Isoquinolines

| R | X | Y |
|---|---|---|
| I | H | H |
| I | F | H |
| I | Cl | H |
| I | CH$_3$ | H |
| I | I | H |
| I | H | CH$_2$F |
| I | F | CH$_2$F |
| I | Cl | CH$_2$F |
| I | CH$_3$ | CH$_2$F |
| SCH$_3$ | I | CH$_2$F |
| SCH$_3$ | H | CH$_2$F |
| SCH$_3$ | F | CH$_2$F |
| SCH$_3$ | Cl | CH$_2$F |
| SCH$_3$ | CH$_3$ | CH$_2$F |
| CH$_2$=CHCH$_2$F | I | H |
| CH$_2$=CHCH$_2$F | H | H |
| CH$_2$=CHCH$_2$F | F | H |
| CH$_2$=CHCH$_2$F | Cl | H |
| CH$_2$=CHCH$_2$F | CH$_3$ | H |

The invention also provides methods for conducting positron emission tomography or single photon emission tomography imaging.

In particular the invention provides a method for conducting positron emission tomography of a subject comprising:

1) administering to the subject an image-generating amount of a compound of Formula I which contains at least one of the following: $^{76}$Br, $^{75}$Br, and $^{18}$F, and 2) measuring the distribution within the subject of the compound by positron emission tomography.

Also provided is a method for conducting single photon emission imaging of a subject comprising:

1) administering to the subject an image-generating amount of a compound of Formula I which contains at least one of the following: $^{82}$Br, $^{77}$Br, $^{123}$I or $^{131}$I, and 2) measuring the distribution within the subject of the compound by single photon emission tomography.

Table 2 shows results of in vitro binding studies of compounds of Formula II, in rat cortical and striatal homogenates.

TABLE 2

Transporter Binding Site Inhibition Data for Various Ligands in Rat Brain Striatial and Cortical Membranes

| R | DA K$_i$ (nM) | NE K$_i$ (nM) | 5-HT K$_i$ (nM) |
|---|---|---|---|
| I (racemic 6, trans) | 14 | 961 | 2.3 |
| Br (racemic 5, trans) | 9.6 | 2390 | 5.1 |
| (Z) —CH=CHCH$_2$F (racemic 19,) trans) | 221 | — | 2.8 |

As seen in Table 2, a preferred compound, trans-1,2,3,5,6,10b-hexahydro-6-[4-iodophenyl]pyrrolo-[2,1-a]isoquinoline (compound 6 in FIGS. 1A and 1E), exhibited high in vitro affinity and good selectivity for the serotonin transporter (Ki=2.3 nM vs. [$^3$H]citalopram (a potent serotonin transporter ligand), Ki=14 nM vs. [3H]WIN 35428 (a potent dopamine transporter ligand), and Ki=961 nM vs. [$^3$H]desmethylimipramine (a potent norepinephrine transporter ligand). A second preferred compound, trans-1,2,3,5, 6,10b-hexahydro-6-[4-bromophenyl]pyrrolo-[2,1-a] isoquinoline (compound 5 in FIGS. 1A, 1D and 1E), exhibited high in vitro affinity for the serotonin transporter (Ki=5.1 nM vs. [$^3$H]citalopram (a potent serotonin transporter ligand), Ki=9.6 nM vs. [$^3$H]WIN 35428 a (potent dopamine transporter ligand) and Ki=2390 nM vs. [$^3$H] desmethylimipramine (a potent norepinephrine transporter ligand). A third preferred compound, trans-1,2,3,5,6,10b-hexahydro-6-[4'Z-(3-fluoro-1-propenyl)phenyl]pyrrolo-[2, 1-a]isoquinoline (compound 19 in FIG. 1D), exhibited high in vitro affinity and selectivity for the serotonin transporter (Ki=2.8 nM vs. [$^3$H]citalopram (a potent serotonin transporter ligand), and Ki=221 nM vs. [$^3$H]WIN 35428 a (potent dopamine transporter ligand). This last compound (trans-1, 2,3,5,6,10b-hexahydro-6-[4'Z-(3-fluoro-1-propenyl)phenyl] pyrrolo-[2,1-a]isoquinoline (compound 19 in FIG. 1D)) is most preferred of the compounds in Table 2 because it shows high affinity for and the most selectivity for the serotonin transporter.

Table 3 shows results of in vitro binding site inhibition studies of compounds of Formula II with various R groups in membranes from dog canine kidney (MDCK) cells which have been stably transfected with cDNA that encodes human dopamine transporters and in membranes from human embryonic kidney cell line (HEK-293) stably transfected with either human serotonin or human norepinephrine transporter.

TABLE 3

Transporter Binding Site Inhibition Data of Various Ligands in Dog Canine Kidney Cells Transfected with cDNA Encoding Human Dopamine, and in Human Embryonic Kidney Cell Line (HEK-293) Stably Transfected with Human Serotonin and Human Norepinephrine Transporter.

| R | DA$^1$, K$_i$ (nM) | NE$^2$, K$_i$ (nM) | 5-HT$^3$, K$_i$ (nM) |
|---|---|---|---|
| I (compound 6, trans) (95% ee) (6S, 10bR) | 0.9 | 10 | 0.9 |
| (Z) —CH=CHCH$_2$F (racemic 19) trans) (6RS, 10bR) | 220 | — | 1.0 |
| racemic C≡CCH$_2$F | 11.3 | 24 | 8.6 |
| racemic SCH$_2$CH$_2$F | | | 5.7 |
| 95% ee (+) SCH$_2$CH$_2$F | | | 2.6 |
| 95% ee (−) SCH$_2$CH$_2$F | | | 6.4 |
| racemic CH$_2$CH$_2$F | | | 13 |
| racemic CH=CH$_2$ | | | 3.7 |
| racemic Br | 0.07 | 2.3 | 0.68 |
| racemic Br, X = F at position 10 | 0.15 | 5.0 | 1.6 |
| —SCH$_3$ | 78 | 69 | 1.0 |
| CIT/RTI-55 | 0.47 | 38.9 | 0.67 |
| Fluvoxamine | — | — | 4.6 |

$^1$[$^3$H]WIN 35428 as reference/control for dopamine transporter site.
$^2$[$^3$H]Nisoxetine as reference/control for norepinephrine transporter site.
$^3$[$^3$H]Citalopram as reference/control for serotonin transporter site.

A preferred compound in Table 3 (also in Table 2) trans-1,2,3,5,6,10b-hexahydro-6-[4-iodophenyl]pyrrolo-[2, 1-a]isoquinoline (compound 6 in FIGS. 1A and 1E), exhibited high in vitro affinity for the serotonin transporter (Ki= 0.9 nM vs. [$^3$H]citalopram (a potent serotonin transporter ligand), Ki=0.9 nM vs. [$^3$H]WIN 35428 (a potent dopamine transporter ligand), and Ki=10 nM vs. [$^3$H]Nisoxetine (a potent norepinephrine transporter ligand). This compound shows high affinity for both serotonin and dopamine transporter sites, and is selective for these two sites versus norepinephrine transporter site. Another preferred compound in Table 3 (also in Table 2) trans-1,2,3,5,6,10b-hexahydro-6-[4'Z-(3-fluoro-1-propenyl)phenyl]pyrrolo-[2, 1-a]isoquinoline (compound 19 in FIG. 1D), exhibited high in vitro affinity and selectivity for the serotonin transporter (Ki=1.0 nM vs. [$^3$H]citalopram (a potent serotonin transporter ligand), and Ki=220 nM vs. [$^3$H]WIN 35428 a (potent dopamine transporter ligand). This compound shows high selectivity and affinity for serotonin transporter sites, compared with dopamine transporter site. In this assay too, this last compound (trans-1,2,3,5,6,10b-hexahydro-6-[4'Z-(3-fluoro-1-propenyl) phenyl]pyrrolo-[2,1-a]isoquinoline (compound 19 in FIG. 1D) is most preferred of the compounds in Table 3 because it shows high affinity for and the most selectivity for the serotonin transporter. Three known compounds in the literature were also measured and reported in Table 3. The first comparative compound has R=-SCH$_3$ and is called McN-5652Z. McN-5652Z exhibited high in vitro affinity and selectivity for the serotonin transporter (Ki=1.0 nM vs. [$^3$H]Citalopram (a potent serotonin transporter ligand), Ki=78 nM vs. [$^3$H]WIN 35428 (a potent dopamine transporter ligand), and Ki=69 nM vs. [$^3$H] Nisoxetine (a potent norepinephrine transporter ligand). This compound shows high affinity and selectivity for serotonin transporter sites. The second comparative compound is RTI-55 (CIT), a tropane (an analogue of cocaine). RTI-55 (CIT) exhibited high in vitro affinity for the serotonin transporter and the dopamine transporter (Ki=0.67 nM vs. [$^3$H]Citalopram (a potent serotonin transporter ligand), Ki=0.47 nM vs. [$^3$H]WIN 35428 (a potent dopamine transporter ligand), and Ki=38.9 nM vs. [$^3$H]Nisoxetine (a potent norepinephrine transporter ligand). This compound shows high affinity for both serotonin and dopamine transporter sites, and is selective for these two sites versus norepinephrine transporter site. The third comparative compound is fluvoxamine. Fluvoxamine exhibited relatively low in vitro affinity (Ki=4.6 nM vs. [$^3$H]Citalopram (a potent serotonin transporter ligand) for the serotonin transporter in comparison to RTI-55 (CIT).

Table 3 indicates that there is comparable binding with compounds containing —C≡CCH$_2$F, —SCH$_2$CH$_2$F, —CH$_2$CH$_2$F, CH=CH$_2$, Br, and Br/10-F (entries 3–10) to serotonin and dopamine. The compound of entry 10 (R=Br/ X=F at position 10) exhibits high affinity and selectivity for the dopamine transporter.

When a preferred compound of this invention (trans-1,2, 3,5,6,10b-hexahydro-6-[4'Z-(3-fluoro-1-propenyl)phenyl] pyrrolo-[2,1-a]isoquinoline (compound 19 in FIG. 1D) is compared with the best-performing art known compound (McN-5652Z) in this assay, each shows very high and equal affinity for the serotonin transporter site, but the 3-fluoro-1-propenylphenyl compound of this invention is more selective than McN-5652Z for the serotonin transporter site, compared to the dopamine transporter site.

Table 4 shows the distribution of radioactivity expressed as percent dose per gram in tissues of unfasted male Sprague Dawley rats at 30 min, 60 min and 120 min after intravenous administration of [$^{123}$I](+)-Trans-1,2,3,5,6,10b-hexaydro-6-[4-iodophenyl]pyrrolo[2,1-a]isoquinoline (Compound 6).

TABLE 4

Regional Distribution of Radioactivity in Tissues of Unfasted
Male Sprague-Dawley Rats Following Intravenous Administration
of 75% ee(+)-(6S, 10bR)-1,2,3,5,6,10b-hexahydro-6-(4'-[$^{123}$I]
iodophenyl)pyrrolo[2,1-a]isoquinoline
Mean % Injected Dose/Gram
(Average of Values for Three Rats)

| Region | 5 min | 30 min | 60 min | 120 min |
|---|---|---|---|---|
| Cerebellum | 1.23 | 0.78 | 0.58 | 0.39 |
| Striatum | 3.43 | 2.46 | 2.28 | 2.06 |
| Hypothalamus | 3.69 | 3.59 | 3.73 | 2.85 |
| Prefrontal Cortex | 5.00 | 3.72 | 3.13 | 2.25 |
| Cortex | 2.06 | 1.60 | 0.89 | 0.74 |
| Striatum/Cereb | 2.9 | 3.2 | 4.0 | 5.3 |
| Hypothal/Cereb | 3.0 | 4.6 | 6.5 | 7.3 |
| PrefCx/Cereb | 4.1 | 4.8 | 5.4 | 5.8 |
| Cortex/Cereb | 1.7 | 2.1 | 1.6 | 1.9 |

[$^{123}$I](+)-Trans-1,2,3,5,6,10b-hexahydro-6-[4-iodophenyl]pyrrolo [2,1-a]isoquinoline showed the greatest accumulation in brain regions rich in serotoninergic neurons with greater hypothalamus to cerebellum ratios (7.3 to 1) at 120 min post injection and prefrontal cortex to cerebellum ratios (5.8 to 1) at 120 min post injection than previously tested SPECT serotonin transporter ligands. The cerebellum contains a very low density of serotonin transporter sites and is taken as "background" in this analysis of regional uptake. The data in Table 4 shows that the known density of serotonin transporter sites in various brain regions is proportional to the concentration of drug uptake in those respective regions. Further, the data in Table 4 show that the ratio of a drug concentration in a given brain region to the concentration in the cerebellum (background) increases with time, showing that the drug binds serotonin transporter sites. These data strongly suggest that the halopyrroloisoquinolines of this invention, e.g. those labeled with $^{18}$F or $^{123}$I, are potential radiopharmaceuticals for the diagnosis of psychiatric disorders such as depression and obsessive-compulsive disorder in humans using emission tomographic techniques.

The radioactively labeled compounds are to be used for diagnosis and imaging; whereas the non-radioactively labeled compounds are to be used for treatment of psychiatric disease, i.e. not cancer.

Table 5 shows the distribution of radioactivity expressed as percent dose per gram in tissues of unfasted male Sprague Dawley rats and ratios after intravenous administration of [$^{123}$I](+)-Trans-1,2,3,5,6,10b-hexaydro-6-[4-iodophenyl]-pyrrolo[2,1-a]isoquinoline with and without prior administration of a serotonin transporter blocker (paroxetine) or dopamine transporter blocker (GBR12909).

TABLE 5

Regional Uptake (% dose/gram) and Ratios of
95% ee(6S, 10bR)-I-McN in Sprague Dawley Rats
(n = 4) at 60 Min Following Preblocking
(5 mg/kg i.v. 15 min prior to radioligand)

| Region | SEROTONIN (paroxetine) | DOPAMINE (GBR 12909) | No Blocker |
|---|---|---|---|
| Cerebellum | 0.43 | 0.55 | 0.46 |
| Striatum | 1.39 | 1.36 | 2.21 |
| Hypothalamus | 2.00 | 3.62 | 3.75 |
| Prefrontal Cortex | 1.98 | 2.8 | 2.3 |
| Cortex | 1.8 | 2.1 | 1.88 |

TABLE 5-continued

Regional Uptake (% dose/gram) and Ratios of
95% ee(6S, 10bR)-I-McN in Sprague Dawley Rats
(n = 4) at 60 Min Following Preblocking
(5 mg/kg i.v. 15 min prior to radioligand)

| Region | SEROTONIN (paroxetine) | DOPAMINE (GBR 12909) | No Blocker |
|---|---|---|---|
| Striatum/Cereb | 3.2 | 2.47 | 4.8 |
| Hypthal/Cereb | 4.65 | 6.6 | 8.15 |
| PrefCx/Cereb | 4.6 | 5.1 | 5.0 |
| Cortex/Cereb | 4.18 | 3.82 | 4.08 |

The data in Table 5 show that the uptake (concentration) of drug in a certain brain region is associated with serotonin transporter sites, as opposed to non-specific binding. For example, in the striatum, both dopamine transporter sites and serotonin transporter sites are binding the drug, evidenced by a substantial decrease in uptake in the presence of paroxetine and GBR12909 (blockers). In the hypothalamus, serotonin transporter sites are more numerous than dopamine transporter sites, and are responsible for drug uptake in this region, as shown by a substantial decrease in drug uptake following paroxetine injection but no decrease follwoing GBR12909 injection.

Table 6 shows the distribution of radioactivity expressed as percent dose per gram in tissues of unfasted male Sprague Dawley rats following intravenous administration of Trans-1,2,3,5,6,10b-hexahydro-6-[4-iodophenyl]-pyrrolo[2,1-a] isoquinoline.

TABLE 6

Distribution of Radioactivity in Tissues of Unfasted Male
Sprague Dawley Rats Following Intravenous Administration
of (+)-Trans-1,2,3,5,6,10b-hexahydro-6-
[4-iodophenyl]-pyrrolo[2,1-a]isoquinoline
Mean % Injected Dose/Gram (Range of 4 rats +/SD)

| Organ | 30 min | 60 min | 120 min |
|---|---|---|---|
| Blood | 0.24 (0.2–0.26) | 0.30 (0.22–0.55) | 0.21 (0.19–0.21) |
| Heart | 0.55 (0.43–0.62) | 0.51 (0.43–0.58) | 0.47 (0.4–0.52) |
| Muscle | 0.27 (0.19–0.33) | 0.26 (0.22–0.33) | 0.27 (0.26–0.3) |
| Lung | 1.53 (1.32–1.79) | 1.28 (1.14–1.51) | 0.92 (0.73–1.12) |
| Kidney | 0.84 (0.76–0.93) | 0.66 (0.6–0.71) | 0.79 (0.74–0.85) |
| Spleen | 1.00 (0.87–1.08) | 0.74 (0.66–0.79) | 0.54 (0.5–0.59) |
| Liver | 1.62 (1.49–1.8) | 1.26 (1.2–1.27) | 1.18 (1.1–1.23) |
| Thyroid | 1.07 (0.54–2.08) | 1.50 (1.05–2.02) | 1.04 (0.86–1.44) |
| Brain | 0.85 (0.77–0.9) | 0.70 (0.63–0.76) | 0.43 (0.43–0.56) |

The data in Table 6 are useful in several ways. 1) The data can be used in art-known computer programs to calculate estimates for human dosages. 2) The compound is metabolically stable. If the iodine were significantly metabolized off the compound, then there would be a much higher uptake of the compound in the thyroid the art, NaI can be oxidized to ICl. In this case the iodine can be a radioactive isotope, e.g. $^{124}$I. $^{124}$ICl can then be reacted with a compound of Formula IV, to yield a compound of Formula I.

Optionally, the kit can include items of apparatus, such as a reaction vessel, device for transferring isotopic material to the reaction vessel, pre-packed separation column for separating product from excess reactants, shielding and the like, as known in the art. See, e.g., Zea-Ponce, U., et al. (1998) *J. Nuclear Med.* 36:525–529.

FIGS. 1A–1E provide exemplary synthetic routes for the compounds of this invention, but are in no way limiting. Modification of the materials and methods can be made by routine choice and without undue experimentation by those of ordinary skill in the art.

by iodination to afford trans-1,2,3,5,6,10b-hexahydro-6-(4'-iodophenyl) pyrrolo [2,1-a]isoquinoline (trans-6). Enantiomeric enriched (+)-(6S, 10bR)-1,2,3,5,6,10b-hexahydro-6-(4'-iodophenyl)pyrrolo[2,1-a]isoquinoline was obtained by the same reaction sequence starting with (+)-2(R)-phenylpyrrolidine.

Figure 1B:
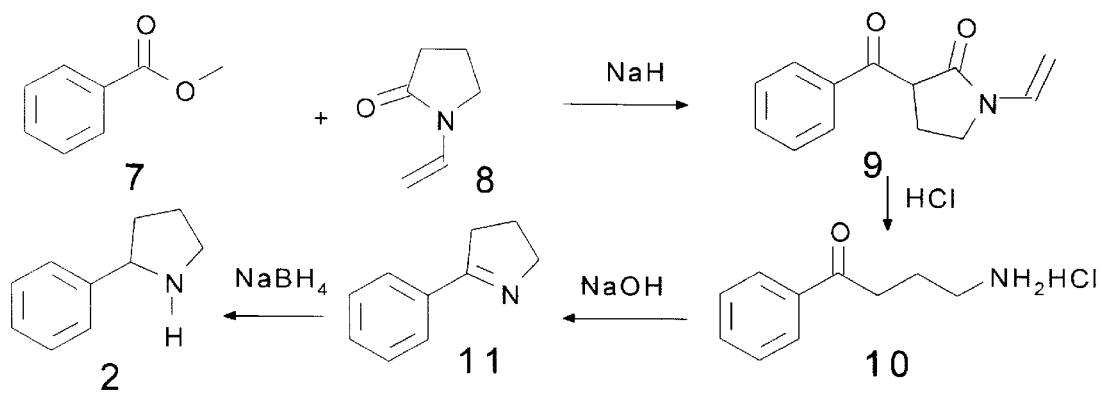

Racemic 2-phenylpyrrolidine was prepared according to the literature outlined in FIG. 1B. (+)-2(R)-

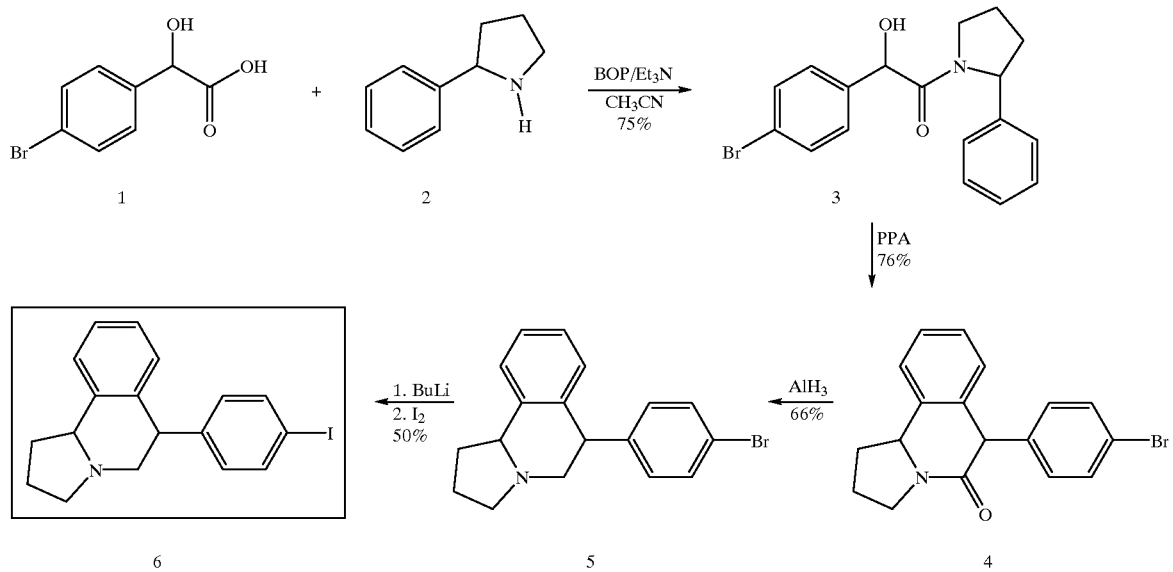

Scheme 1

Figure 1C:
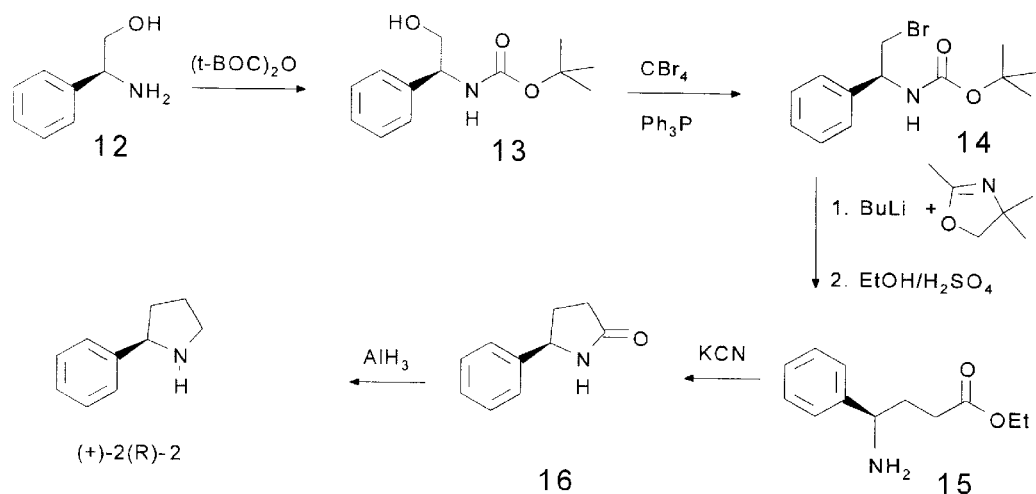

Phenylpyrrolidine was prepared starting with (+)-2(S)-phenylglycinol (12) as outlined in FIG. 1C. The commercially available (+)-2(S)-phenylglycinol was first tert-BOC protected and then brominated to provide N-(tert-butoxycarbonyl)-2(S)-phenylglycinbromide (14), which was then coupled with lithiated 2,4,4-trimethyl-2-oxazoline followed by acid ethanolysis to yield ethyl 4(R)-amino-4-phenylbutyrate (15). This y-aminoester was then catalytically cyclized20 to form (+)-5(R)-phenyl-2-pyrrolidinone (16), which was then reduced with an alane ($AlH_3$) solution to yield (+)-2(R)-phenylpyrrolidine ((+)-2(R)-2). This new procedure gave the desired product with >95% enantiomeric excess in an overall 45% yield.

Figure 1D:
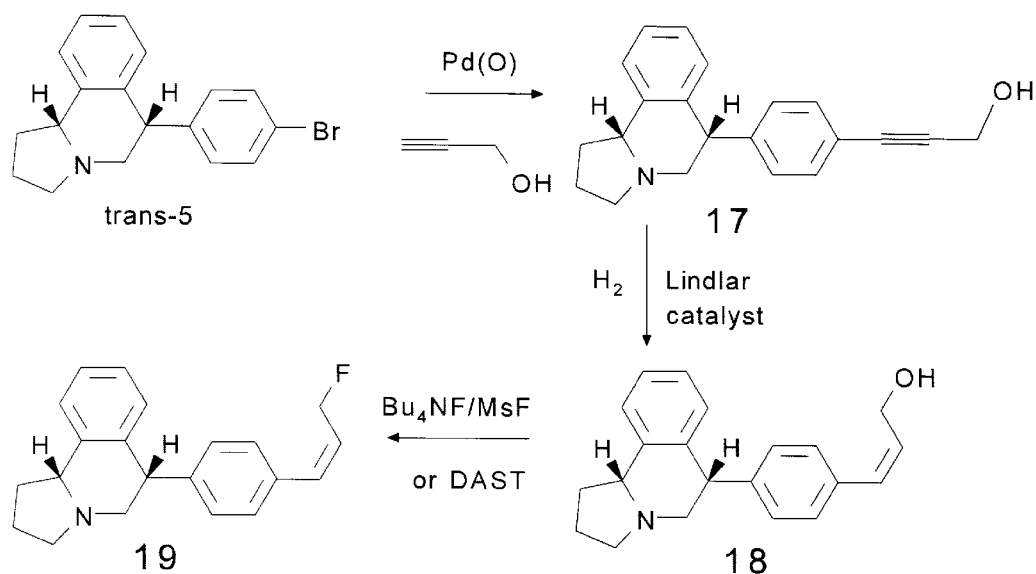

Trans-6-[4'-(3-Fluoro-l(Z)-propenyl)phenyl]-1,2,3,5,6, 10b-Hexahydropyrrolo[2,1-a]isoquinoline (19) was prepared in a three step procedure starting with trans-5 as outlined in FIG. 1D.

Figure 1E:
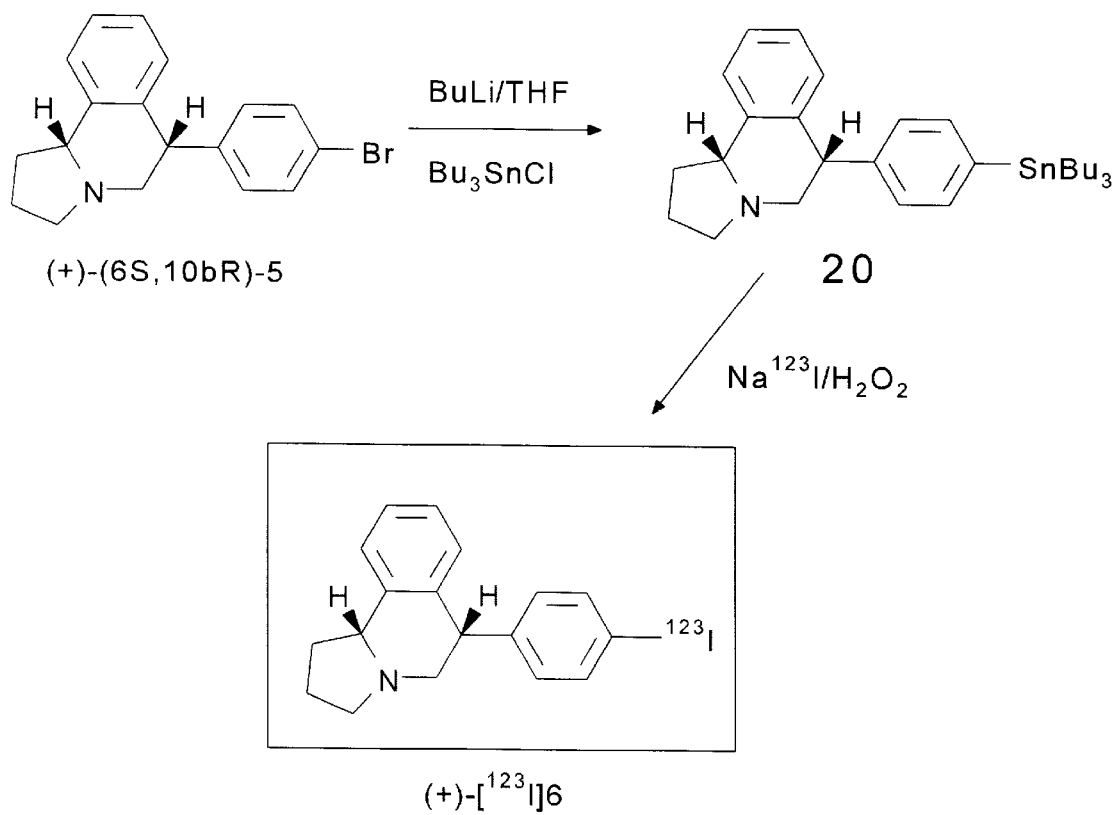

Radiochemical Synthesis (+)-(6S, 10bR)-1,2,3,5,6,10b-Hexahydro-6-(4'-[$^{123}$I] iodophenyl)pyrrolo[2,1-a]isoquinoline was prepared from a tributyltin precursor as outlined in FIG. 1E. Enantiomeric enriched (50% ee) (+)-(6S, 10bR)-6-(4'-bromophenyl)-1,2, 3,5,6,10b-hexahydropyrrolo[2,1-a]isoquinoline ((+)-(6S, 10bR)-5) was allowed to react with butyllithium and then treated with tributyltin chloride to afford the tributyltin precursor (20) which was further enriched by using Regis (S, S)Whelk-O chiral column HPLC separation. The highly enriched (75% ee) tributyltin precursor (0.5 mg) was treated with 6.1 mCi sodium [$^{123}$I]iodide (NCA), 0.1 N HCl (100 μL) followed by addition of 50 μL of 3% $H_2O_2$. The reaction mixture was quenched with 100 μL of 30% aqueous sodium bisulfite solution and then neutralized with 1.0 mL of It will be understood that compounds of the invention can be labeled with an isotope of any atom or combination of atoms in the structure. While [$^{18}$F] and [$^{123}$I] have been emphasized herein as being particularly useful for PET or SPECT imaging, other uses are contemplateed and will be apparent to those skilled in the art. For example, without limitation, compounds of the invention can be labeled with [$^{14}$C] to provide a tracer useful for biochemical studies of dopamine transporter. In addition, the binding studies reported herein demonstrate a pharmacological effect of compounds of the invention which ca be utilized for physiological and behavioral studies and therapies, as will be apparent to those skilled in the art.

All references cited in this application are specifically incorporated in their entirety by reference herein.

The following examples illustrate the invention but are in no way intended to limit the scope of the invention.

EXAMPLES

Chemical Synthesis

Trans-1,2,3,5,6,10b-hexahydro-6-(4'-iodophenyl)pyrrolo [2,1-a]isoquinoline (trans-6), was synthesized by a four step reaction sequence outlined in FIG. 1A. 4-Bromomandelic acid (1) was coupled with 2-phenylpyrrolidine (2) in the presence of BOP reagent to yield 2-phenylpyrrolidino 4-bromophenyl-α-hydroxyacetate (3). Upon treatment with PPA, the amide 3 was cyclized to the lactam (4) which was reduced with aluminum hydride to provide a pair of diastereomers (5) with a trans-to-cis ratio of 2. The desired trans-6-(4'-bromophenol)-1,2,3,5,6,10b-hexahydropyrrolo [2,1-a]-isoquinoline (trans 5) was separated by flash chromatography. Trans-5 was treated with butyllithium followed saturated NaHCO₃ solution. The resulting solution was loaded on a preconditioned C$_{18}$ Sep-Pak and then rinsed with 10 mL of water. Elution with 10 mL of 85% MeOH, 0.1% Et₃N in water followed by HPLC purification on a Waters Nova-Pak C$_{18}$ (8×200 mm with 80:20:0.1 CH₃OH:H₂O:Et₃N, flow rate 3.0 mL/min, Rt 16 min) afforded 1.52 mCi 75% ee (+)-(6S, 10bR)-1,2,3,5,6,10b-hexahydro-6-(4'-[$^{123}$I]iodophenyl)pyrrolo[2,1-a]-isoquinoline in 25% radiochemical yield E.O.S. in a total synthesis time of 3 h. Radio-TLC (SiO₂ 95:5 CH₂Cl₂:MeOH, Rf 0.42) and radio-HPLC analysis (Nova-Pak C$_{18}$ 3.9×150 mm, 80:20:0.1 CH₃OH:H₂O:Et₃N, flow rate 1.0 mL/min, Rt 9.6 min) showed [(+)-(6S, 10bR)-1,2, 3,5,6,10b-hexahydro-6-(4'-[$^{123}$I]iodophenyl)pyrrolo[2,1-a]-lisoquinoline ((+)-[$^{123}$I]6), was >98% radiochemically pure with a specific activity of 1.19 Ci/μmol. The radioactivity was concentrated under reduced pressure, dissolved in sterile saline with 5% EtOH, and filtered through a Gelman 0.2 micron filter for use in in vivo studies.

Experimental Section

General Remarks. ¹H and ¹³C NMR spectra were obtained with a GE 300 MHz instrument, and chemical shifts are reported in ppm on the δ scale with the TMS as an internal reference. Column chromatography separations were performed with Merck brand Silica gel 60, 230–400 mesh. Mass spectral analyses were performed by Emory University Mass Spectrometry Facility, Atlanta, Ga. Elemental analyses were performed by Atlantic Microlab, Inc. (Norcross, Ga.).

Materials. Commercially available reagents were used without further purification unless stated otherwise. Racemic 2-Phenylpyrrolidine was prepared from N-vinyl-2-pyrrolidinone and methyl benzoate.[16] (+)-2(R)-Phenylpyrrolidine prepared from (+)-2(S)-phenylglycinol[18] was about 90% enantiomeric excess estimated by ¹H NMR integration of the Mosher's salt.

6-(4'-Bromophenyl)-1,2,3,5,6,10b-hexahydropyrrolo[2,1-a]isoquinolin-5-one (4).

To a stirred solution of 4-bromomandelic acid (832 mg, 3.6 mmol), 2-phenylpyrrolidine (530 mg, 3.6 mmol), BOP reagent (benzotriazol-1-yloxytris(dimethylamino) phosphonium hexafluorophosphate, 1.53 g, 3.6 mmol) in 25 mL of anhydrous acetonitrile was added triethylamine (1.06 mL, 7.2 mmol) at room temperature under an argon atmosphere. The reaction mixture was stirred at room temperature for 4 h, concentrated under reduced pressure, then dissolved in methylene chloride (50 mL). The methylene chloride solution was washed with 1N HCl solution, water, saturated sodium bicarbonate solution, water, brine, and dried over anhydrous MgSO₄, concentrated under reduced pressure to afford a syrup in a flask. PPA (polyphosphoric acid, 10 g) was added to the flask. The reaction mixture was heated on a rotavap in boiling water bath for 1 h, cooled to room temperature, solublized in ice water, extracted with methylene chloride (4×15 mL). The methylene chloride extract was washed with saturated sodium bicarbonate solution, water, brine, and dried over anhydrous MgSO₄, concentrated under reduced pressure to afford a crude product mixture. Flash chromatography (silica gel, 0.5% MeOH, 0.01% Et₃N in methylene chloride) to afford 860 mg of 4 (70% yield for two steps) as a mixture of trans and cis isomers with trans to cis ratio 2:1 (estimated by ¹H NMR integration). Recrystallization with THF isolated trans isomer as a yellow solid, mp 204–206° C. ¹H NMR (CDCl₃) δ 1.96–2.22 (m, 3H, C2H₂ & C1H), 2.66–2.78 (m, 1H, C1H), 3.48–3.58 (m, 1H, C3H), 3.732 (dd, 1H, J=7.5, 11.7 Hz, C3H), 4.610 (s, 1H, C6H), 4.64–4.70 (m, 1H, C10bH), 6.591 (d, 1H, J=7.8 Hz, aryl), 7.104 (d, 2H, J=8.1 Hz, C6 phenyl aryl), 7.12–7.28 (m, 3H, 8, 9, aryl), 7.520 (d, 2H, J=8.4 Hz, C6 phenyl aryl); ¹³C NMR (CDCl₃) δ 23.06 (C2), 31.21 (C1), 45.07 (C3), 52.99 (C10b), 58.62 (C6), 121.10 (C4'), 123.58 (aromatic), 126.74 (aromatic), 127.38 (aromatic), 131.38 (aromatic), 132.60 (aromatic), 136.15 (aromatic), 136.55 (aromatic), 136.79 (aromatic), 167.36 (C5). HRMS calculated 341.0415 (for C$_{18}$H$_{16}$NOBr), measured 341.0427 (relative error 3.4 ppm).

6-(4'-Bromophenyl)-1,2,3,5,6,10b-hexahydropyrrolo[2,1-a]-isoquinoline (5).

To a cooled (0° C.) anhydrous aluminum chloride (550 mg, 4.2 mmol) was added anhydrous THF (10 mL) via syringe under an argon atmosphere. After 5 minute stirring at 0° C., a 1.0 M LiAlH₄ solution in THF (12.6 mL, 12.6 mmol) was added. The resulting cloudy solution was allowed to warm to room temperature and stirred for 20 min to give the alane solution. To this stirred alane solution was added a solution of 1,2,3,5,6,10b-Hexahydro-6-(4'-bromophenyl])pyrrolo[2,1-a]isoquinolin-5-one (720 mg, 2.1 mmol) in 15 mL of THF at −78° C. under an argon atmosphere. The reaction mixture was stirred at −78° C. for 1 hr and then at room temperature for 1 h, recooled to 0° C. and quenched with 1 N HCl solution (15 mL). The resulting slurry was extracted with ether (4×20 mL). The combined ethereal extract was washed with saturated NaHCO₃solution, water, brine, and dried over anhydrous MgSO₄ and concentrated to afford a product mixture. Flash chromatography (silica, 2.5% MeOH, 0.05% Et₃N in methylene chloride) afforded cis-5 176 mg (25% yield) and trans-5 330 mg (48% yield), total yield 73% with trans to cis ratio of 2:1. HRMS calculated 327.0623 (for C$_{18}$H$_{18}$NBr), measured 327.0626 (relative error 1.0 ppm).

Cis-6-(4'-Bromophenyl)-1,2,3,5,6,10b-hexahydropyrrolo[2,1-a]-isoquinoline (cis-5).

This product was isolated as a thick brown oil. ¹H NMR (CDCl₃) δ 1.71–2.02 (m, 3H, C2H₂ & C1H), 2.37–2.65 (m, 3H, C1H, C3H & C5H), 3.119 (ddd, 1H, J=4.2, 4.2, 7.8 Hz, C3H), 3.416 (dd, 1H, J=6.6, 11.7 Hz, C5H), 3.558 (dd, 1H, J=7.5, 8.4 Hz, C10bH), 4.355 (dd, 1H, J=6.6, 10.5 Hz, C6H), 6.795 (d, 1H, J=7.8 Hz, aryl), 7.044 (d, 2H, J=8.4 Hz, C6 phenyl aryl), 7.07–7.20 (m, 3H, aryl), 7.411 (d, 2H, J=8.4 Hz, C6 phenyl aryl); ¹³C NMR (CDCl₃) δ 21.87 (C2), 30.30 (C1), 44.66 (C3), 52.88 (C10b), 57.79 (C6), 63.67 (C5), 120.16 (4'C), 125.17 (aromatic), 126.20, 128.83, 130.72, 131.35, 136.86, 139.12, 143.25.

Trans-6-(4'-Bromophenyl)-1,2,3,5,6,10b-hexahydropyrrolo[2,1-a]isoquinoline (trans-5).

This product was isolated as a thick brown oil. ¹H NMR (CDCl₃) δ 1.72–2.02 (m, 3H, C2H₂ & C1H), 2.28–2.40 (m, 1H, C1H), 2.514 (dt, 1H, J=9.3, 8.7 Hz, C5H), 2.836 (dd, 1H, J=5.1, 11.1 Hz, C5H), 2.893.03 (m, 2H, C3H₂), 3.417 (dd, 1H, J=6.9, 9.3 Hz, C10bH), 4.109 (t, 1H, J=4.8 Hz, C6H), 6.854 (d, 1H, J=7.8 Hz, aryl), 7.02–7.18 (m, 5H, aryl), 7.342 (d, 2H, J=8.4 Hz, C6 phenyl aryl); ¹³C NMR (CDCl₃) δ 22.08 (C2), 30.11 (C1), 45.46 (C3), 53.93 (C10b), 56.08 (C6), 63.78 (C5), 119.96 (4'C), 125.57 (aromatic), 126.11, 129.31, 130.53, 131.08, 136.65, 138.91, 145.50.

Trans-1,2,3,5,6,10b-Hexahydro-6-(4'-iodophenyl)pyrrolo[2,1-a]isoquinoline (trans-6).

To a stirred solution of 1.6 M of butyllithium (0.63 mL, 1.0 mmol) in hexane was added slowly a solution of trans-1,2,3,5,6,10b-hexahydro-6-(4'-bromophenyl)pyrrolo[2,1-a]isoquinoline (100 mg, 0.3 mmol) in 5 mL of anhydrous THF at −78° C. under an argon atmosphere. After stirred at −78° C. for 5 min., a solution of iodine (252 mg, 1.0 mmol) in 5 mL of anhydrous. THF was added in one portion. The reaction mixture was stirred at −78° C. for 30 min and then at room temperature for further 15 min, quenched with ice-water (20 mL), extracted with methylene chloride (3×20 mL). The combined methylene chloride extract was washed with 10% sodium bisulfite solution, water, brine, dried over anhydrous MgSO$_4$, filtered and concentrated to afford a yellow oil. Flash chromatography with 2.5% MeOH, 0.05% Et$_3$N in methylene chloride gave 55 mg of thick colorless oil (50% yield). $^1$H NMR (CDCl$_3$) δ 1.73–2.05 (m, 3H, C2H$_2$ & C1H), 2.30–2.2.44 (m, 1H, C1H), 2.579 (dt, 1H, J=9.0, 8.7 Hz, C3H), 2.869 (dd, 1H, J=5.1, 11.1 Hz, C5H), 2.90–3.03 (m, 2H, C3H & C5H), 3.480 (dd, 1H, J=7.2, 9.0 Hz, C10bH), 4.125 (t, 1H, J=4.8 Hz, C6H), 6.865 (d, 1H, J=7.5 Hz, aryl), 6.995 (d, 2H, J=8.1 Hz, C6 phenyl aryl), 7.04–7.20 (m, 3H, aryl), 7.575 (d, 2H, J=8.1 Hz, C6 phenyl aryl); $^{13}$C NMR (CDCl$_3$) δ 22.17 (C2), 30.31 (C1), 45.48 (C3), 54.13 (C10b), 55.95 (C6), 63.67 (C5), 91.60 (4'C), 125.73 (aromatic), 126.30, 129.30, 130.97, 137.23. HRMS calculated 375.0484 (for C$_{18}$H$_{18}$NI), measured 375.0490 (relative error 1.6 ppm).

N-(tert-Butoxycarbonyl)-2(S)-phenylglycinol (13).

To a stirred solution of (+)-2(S)-phenylglycinol (1.4 g, 10 mmol) and di-tert-butyldicarbonate (2.4 g, 11 mmol) in 50 mL of anhydrous methylene chloride was added triethylamine (1.7 mL, 11 mmol) at room temperature. The reaction mixture was stirred at room temperature for 12 h, concentrated under reduced pressure to afford a crude product mixture. Flash chromatography (silica gel, 1.5% MeOH, 0.03% Et$_3$N in methylene chloride) afforded 2.20 g of product (92% yield) as a white solid, mp 135–137° C. $^1$H NMR (CDCl$_3$) δ 1.416 (s, 9H, tert-Bu), 3.060 (s, 1H, OH), 3.759 (s, 2H, OCH$_2$), 4.736 (s, 1H, NH), 5.444 (s, 1H, benzyl), 7.22–7.32 (m, 5H, aryl); $^{13}$C NMR (CDCl$_3$) δ 28.25 (CH$_3$), 56.73 (CMe$_3$), 66.40 (OCH$_2$), 79.85 (NCH), 126.48 (aromatic), 127.47 (aromatic), 128.55 (aromatic), 156.13 (aromatic). Elemental analysis calculated for C$_{13}$H$_{19}$NO$_3$ C: 65.80, H: 8.07, N: 5.90; measured C: 65.75, H: 8.06, N: 5.86.

N-(tert-Butoxycarbonyl)-2(S)-phenylglycinbromide (14).

To a stirred solution of N-(tert-butoxycarbonyl)-2(S)-phenylglycinol (1.67 g, 7.0 mmol) and carbon tetrabromide (5.0 g, 15 mmol) in 35 mL of anhydrous ether was added a solution of triphenylphosphine (4.09 g, 15.4 mmol) in 25 mL of anhydrous ether at 0° C. The reaction mixture was stirred at room temperature for 12 h. The ether suspension was filtered with a sintered glass funnel containing a bed of celite. The ether filtrate was concentrated under reduced pressure to give a crude product. Flash chromatography (silica gel, 0.2% MeOH, 0.004% Et$_3$N, 40% methylene chloride in hexane) afforded 1.68 g of product (80% yield) as a white solid, mp 108–109° C. $^1$H NMR (CDCl$_3$) δ 1.431 (s, 9H, tert-Bu) 3.664 (s, 2H, BrCH$_2$), 5.001 (s, 1H, NH), 5.272 (d, 1H, J=7.8 Hz, benzyl), 7.25–7.38 (m, 5H, aryl); $^{13}$C NMR (CDCl$_3$) δ 28.24 (CH$_3$) 37.00 (BrCH$_2$), 54.80 (CMe$_3$), 79.98 (NCH), 126.35 (aromatic), 127.88, 128.59, 139.40, 154.91.

Ethyl 4(R)-amino-4-phenylbutyrate (15).

To a stirred solution of 2,4,4-trimethyl-2-oxazoline (620 μL, 4.8 mmol) in 10 mL of anhydrous tetrahydrofuran was added a 2.5 M solution of butyllithium (1.76 mL, 4.4 mmol) in hexane at −78° C. under an argon atmosphere. The reaction mixture was stirred at −78° C. for 30 min. A solution of N-(tert-Butoxycarbonyl)-2-(S) phenylglycinbromide (14) (1.08 g, 3.6 mmol) in 25 mL of anhydrous THF was added dropwise over a period of 10 min. The reaction mixture was stirred at −78° C. for 30 min, then at room temperature for 45 min, quenched with cold saturated sodium chloride aqueous solution, extracted with ether (5×5 mL). The combined ether extracts were washed with water, brine, dried over anhydrous MgSO$_4$, concentrated under reduced pressure to give a crude 4,4-dimethyl-2-[3(R)-phenyl-3-(tert-butoxycarbamidyl)propyl-2-oxazoline. $^1$H NMR (CDCl$_3$) δ 1.256 (s, 6H, 2CH$_3$), 1.398 (s, 9H, tert-Bu), 2.05–2.35 (m, 4H), 3.879 (s, 2H), 4.670 (d, 1H, J=3.6 Hz), 5.614 (d, 1H, J=7.2 Hz), 7.20–7.34 (m, 5H); $^{13}$C NMR (CDCl$_3$) δ 24.97, 28.18, 32.52, 54.68, 66.72, 78.80, 126.03, 126.95, 128.32, 142.34, 155.09, 165.53. To a stirred solution of this crude 4,4-dimethyl-2-[3(R)-phenyl-3-(tert-butoxycarbamidyl)propyl-2-oxazoline (1.0 g, 3.01 mmol) in 20 mL of 95% ethanol was added a solution of 2.0 mL of concentrated sulfuric acid in 18 mL of 95% ethanol at room temperature. The reaction mixture was heated to reflux for 15 h, cooled to room temperature, concentrated at reduced pressure. The residue was neutralized with 5% sodium bicarbonate solution, then basified with saturated sodium carbonate solution, extracted with methylene chloride (4×20 mL). The combined methylene chloride extracts were washed with brine, dried over anhydrous MgSO$_4$, concentrated under reduced pressure to give 580 mg of product (76% yield for two steps) as a thick oil. $^1$H NMR (CDCl$_3$) δ 1.220 (t, 3H, J=7.2 Hz, CH$_3$), 1.694 (br, 2H, NH$_2$), 1.92–2.04 (m, 2H), 2.24–2.34 (m, 2H), 3.901 (t, 1H, J=6.9 Hz, benzyl), 4.082 (q, 2H, J=7.2 Hz, OCH$^2$), 7.20–7.45 (m, 5H, aryl); $^{13}$C NMR (CDCl$_3$) δ 14.00, 31.11, 34.13, 55.25, 60.08, 126.08, 126.93, 128.33, 145.44, 173.25.

5(R)-phenyl-2-pyrrolidinone (16).

To a stirred solution of ethyl 4(R)-amino-4-phenylbutyrate (515 mg, 2.48 mmol) in 20 mL of anhydrous methanol was added sodium cyanide (25 mg, 0.5 mmol) at room temperature. The reaction mixture was stirred at 55° C. for 4 h, cooled to room temperature, concentrated under reduced pressure. The residue was taken up in methylene chloride, washed with water, brine, dried over anhydrous MgSO$_4$, concentrated to afford 391 mg of product (98% yield) as a colorless crystal, mp 103–105° C. (lit.[17] 102–104° C.). $^1$H NMR (CDCl$_3$) δ 1.80–1.95 (m, 1H), 2.27–2.42 (m, 2H), 2.45–2.58 (m, 1H), 4.709 (t, 1H, J=7.2 Hz), 7.22–7.38 (m, 5H), 7.425 (br, 1H); $^{13}$C NMR (CDCl$_3$) δ 30.19, 30.93, 57.91, 125.34, 127.46, 128.56, 142.43, 178.85.

Trans-1,2,3,5,6,10b-Hexahydro-6-[4'-(3-hydroxy-1-propenyl)phenyl]pyrrolo[2,1-a]isoquinoline (17).

To a stirred solution of Pd(OAc)$_2$ (17 mg, 0.07 mmol), Ph$_3$P (35 mg, 0.14 mmol), CuI (15 mg), Pd(Ph$_3$P)$_4$ (10 mg) in 5 mL of triethylamine was added a solution of trans-1,2,3,5,6,10b-hexahydro-6-(4'-bromophenyl)pyrrolo[2,1-a] isoquinoline (440 mg, 1.34 mmol) in 15 mL of triethylamine at room temperature followed by addition of propargyl alcohol (208 mg, 3.67 mmol). The reaction mixture was teated at reflux overnight, cooled to room temperature, quenched with sat'd NaHCO$_3$ solution (20 mL), extracted with methylene chloride (3×20 mL). The combined methylene chloride extract was dried over anhydrous MgSO$_4$, filtered and concentrated to afford a crude product mixture. Flash chromatography with 3.5% MeOH, 0.07% Et$_3$N in methylene chloride gave starting material 280 mg (64% recovery) and 58 mg of thick orange oil (58% conversion yield). $^1$H NMR (CDCl$_3$) δ 1.73–2.05 (m, 3H, C2H$_2$ & C1H), 2.30–2.2.44 (m, 1H, C1H), 2.579 (dt, 1H, J=9.0, 8.7 Hz, C3H), 2.869 (dd, 1H, J=5.1, 11.1 Hz, C5H), 2.90–3.03 (m, 2H, C3H & C5H), 3.480 (dd, 1H, J=7.2, 9.0 Hz, C10bH), 4.125 (t, 1H, J=4.8 Hz, C6H), 6.865 (d, 1H, J=7.5 Hz, aryl), 6.995 (d, 2H, J=8.1 Hz, C6 phenyl aryl), 7.04–7.20 (m, 3H, aryl), 7.575 (d, 2H, J=8.1 Hz, C6 phenyl aryl); $^{13}$C NMR (CDCl$_3$) δ 22.17 (C2), 30.31 (C1), 45.48 (C3), 54.13

(C10b), 55.95 (C6), 63.67 (C5), 91.60 (4'C), 125.73 (aromatic), 126.30, 129.30, 130.97, 137.23.

Trans-1,2,3,5,6,10b-Hexahydro-6-[4'-(3-hydroxy-1(Z)-propenyl)phenyl]pyrrolo[2,1-a]isoquinoline (18).

To a stirred solution of trans-1,2,3,5,6,10b-Hexahydro-6-[4'-(3-hydroxy-1-propynyl)phenyl]pyrrolo[2,1-a]isoquinoline (17) (154 mg, 0.507 mmol) in 10 mL of absolute ethanol was added the Lindlar catalyst (15 mg) at room temperature followed by addition of 7 mg of quinoline. The reaction mixture was stirred under hydrogen at room temperature for 12 h, filtered through a sintered glass funnel with celite, rinsed with methylene chloride (2×10 mL). The filtrate was concentrated to afford a crude product. Flash chromatography with 3.75% MeOH, 0.075% $Et_3N$ in methylene chloride gave 98 mg of thick red oil (63% yield). $^1$H NMR ($CDCl_3$) δ 1.73–2.05 (m, 3H, $C2H_2$ & C1H), 2.30–2.2.44 (m, 1H, C1H), 2.579 (dt, 1H, J=9.0, 8.7 Hz, C3H), 2.869 (dd, 1H, J=5.1, 11.1 Hz, C5H), 2.90–3.03 (m, 2H, C3H & C5H), 3.480 (dd, 1H, J=7.2, 9.0 Hz, C10bH), 4.125 (t, 1H, J=4.8 Hz, C6H), 6.865 (d, 1H, J=7.5 Hz, aryl), 6.995 (d, 2H, J=8.1 Hz, C6 phenyl aryl), 7.04–7.20 (m, 3H, aryl), 7.575 (d, 2H, J=8.1 Hz, C6 phenyl aryl); $^{13}$C NMR ($CDCl_3$) δ 22.17 (C2), 30.31 (C1), 45.48 (C3), 54.13 (C10b), 55.95 (C6), 63.67 (C5), 91.60 (4'C), 125.73 (aromatic), 126.30, 129.30, 130.97, 137.23.

Trans-6-[4'-(3-Fluoro-1(Z)-propenyl)phenyl]-1,2,3,5,6,10b-Hexahydropyrrolo[2,1-a]isoquinoline (19).

To a stirred solution of 1.0 M tetrabutylamonium fluoride (0.45 mL, 0.45 mmol) in 2.0 mL of THF in the presence of molecular sieves (4 Å, 1.0 g) was added a mixture of methylsufonyl fluoride (21 μL, 0.30 mmol) and trans-1,2,3,5,6,10b-Hexahydro-6-[4'-(3-hydroxy-1(Z)-propenyl)phenyl]pyrrolo[2,1-a]isoquinoline (18) (23 mg, 0.075 mmol) in 5 mL of THF at room temperature. The reaction mixture was heated at reflux for 16 h, cooled to room temperature, filtered through a sintered glass funnel with aid of a small amount of methylene chloride (10 mL) and ethyl acetate (10 mL). The filtrate was concentrated to afford a crude product. Flash chromatography with 2.3% MeOH, 0.046% $Et_3N$ in methylene chloride gave 10 mg of thick colorless oil (43% yield). $^1$H NMR ($CDCl_3$) δ 1.73–2.05 (m, 3H, $C2H_2$ & C1H), 2.30–2.2.44 (m, 1H, C1H), 2.579 (dt, 1H, J=9.0, 8.7 Hz, C3H), 2.869 (dd, 1H, J=5.1, 11.1 Hz, C5H), 2.90–3.03 (m, 2H, C3H & C5H), 3.480 (dd, 1H, J=7.2, 9.0 Hz, C10bH), 4.125 (t, 1H, J=4.8 Hz, C6H), 6.865 (d, 1H, J=7.5 Hz, aryl), 6.995 (d, 2H, J=8.1 Hz, C6 phenyl aryl), 7.04–7.20 (m, 3H, aryl), 7.575 (d, 2H, J=8.1 Hz, C6 phenyl aryl) (aromatic), 126.30, 129.30, 130.97, 137.23.

(+)-2(R)-Phenylpyrrolidine ((+)-2(R)-2).

To a cooled (0° C.) anhydrous aluminum chloride (208 mg, 1.56 mmol) was added anhydrous THF (10 mL) via syringe under an argon atmosphere. After 5 min of stirring at 0° C., a 1.0 M $LiAlH_4$ solution in THF (4.68 mL, 4.68 mmol) was added. The resulting cloudy solution was allowed to warm to room temperature and stirred for 20 minutes to give the alane solution. To this stirred alane solution at −78° C. was added a solution of 5(R)-phenyl-2-pyrrolidinone (160 mg, 1.0 mmol) in 10 mL of THF under an argon atmosphere. The reaction mixture was stirred at −78° C. for 1 h. and then at room temperature for 12 h, recooled to 0° C. and quenched with 1 N HCl solution (5 mL). The resulting slurry was diluted with 20 mL of water, basified with 3 N aqueous sodium hydroxide solution to pH 12, extracted with methylene chloride (4×20 mL). The combined organic extract was washed with brine, dried over anhydrous $MgSO_4$, concentrated to afford a crude product. Bulb to bulb distillation with Kugelröhr (88° C./0.9 mmHg) gave 120 mg of product (82% yield) as a colorless oil, $^1$H NMR ($CDCl_3$) δ 1.57–1.71 (m, 1H),1.74–1.96 (m, 2H), 2.101 (s, 1H), 2.11–2.22 (m, 1H), 2.972 (ddd, J=6.9, 8.1, 9.9 Hz, 1H, NCH), 3.172 (ddd, J=5.4, 7.5, 10.2 Hz, 1H, NCH), 4.073 (t, J=7.5 Hz, 1H, benzyl), 7.16–7.40 (m, 5H, aryl); $^{13}$C NMR ($CDCl_3$) δ 25.39 (C4), 34.15 (C3), 46.78 (C5), 62.37 (C2), 126.29 (aromatic), 126.52, 128.11, 144.65.

Trans-1,2,3,5,6,10b-Hexahydro-6-(4'-tributylstannylphenyl)pyrrolo[2,1-a]isoquinoline (10).

To a stirred solution of 2.5 M of butyllithium (0.5 mL, 1.25 mmol) in hexane was added slowly a solution of trans-1,2,3,5,6,10b-hexahydro-6-(4'-bromophenyl)pyrrolo[2,1-a]isoquinoline (191 mg, 0.58 mmol) in 10 mL of anhydrous THF at −78° C. under an argon atmosphere. After stirred at −78° C. for 5 min., tributyltin chloride (350 μL, 1.26 mmol) was added in one portion. The reaction mixture was stirred at −78° C. for 30 min and then at room temperature for further 30 min, quenched with saturated $NaHCO_3$ (30 mL), extracted with diethyl ether (3×20 mL). The combined ethereal extract was washed with water, and dried over anhydrous $MgSO_4$, filtered and concentrated to afford a crude product. Flash chromatography with 2.5% MeOH, 0.05% $Et_3N$ in methylene chloride gave 193 mg of colorless oil (61% yield). $^1$H NMR ($CDCl_3$) δ 0.879 (t, 9H, J=7.2 Hz, $(CH_3)_3$), 1.027 (t, 6H, J=8.1 Hz, $Sn(CH_2)_3$), 1.325 (tq, 6H, J=7.2, 7.2 Hz, $(CH_2Me)_3$), 1.48–1.60 (m, 6H, $(CH_2)_3$), 1.75–2.02 (m, 3H, $C2H_2$ & C1H), 2.28–2.40 (m, 1H, C1H), 2.650 (dt, 1H, J=9.3, 8.7 Hz, C3H), 2.885 (dd, 1H, J=5.1, 11.1 Hz, C5H), 2.92–3.02 (m, 1H, C3H), 3.044 (dd, 1H, J=5.4, 11.1 Hz, C5H), 3.570 (dd, 1H, J=6.9, 9.3 Hz, C10bH), 4.153 (t, 1H, J=5.1 Hz, C6H), 6.909 (d, 1H, J=7.5 Hz, aryl), 7.02–7.15 (m, 3H, aryl), 7.192 (d, 2H, J=7.5 Hz, C6 phenyl aryl), 7.350 (d, 2H, J=7.8 Hz, C6 phenyl aryl); $^{13}$C NMR ($CDCl_3$) δ 9.50 (SnC), 13.63 ($CH_3$), 22.32 (C2), 27.35, 29.05, 30.56 (C1), 45.91 (C3), 54.40 (C10b), 55.95 (C6), 63.44 (C5), 125.74 (C4'), 126.01 (aromatic), 126.08, 128.50, 129.26, 136.34, 137.29, 138.37, 139.41, 144.99. HRMS (FAB) calculated 540.2652 (for $C_{30}H_{46}NSn$, M+H$^+$), measured 540.2641 (relative error −2.1 ppm).

What is claimed is:

1. A compound of the formula:

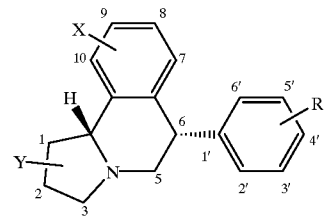

wherein X, Y and R, independently of one another, is each a H; halogen, wherein said halogen is selected from the group consisting of $^{123}$I, $^{124}$I, $^{125}$I, $^{131}$I, $^{75}$Br, $^{76}$Br, $^{77}$Br, $^{82}$Br, $^{18}$F, and $^{210}$At; small alkyl, small alkenyl, or small alkynyl, any of which contains from one to about 6 carbon atoms and optionally having a carbon atom replaced by an O or S; or halogen substituted-small alkyl, halogen substituted-small alkenyl, or halogen substituted-small alkynyl wherein said compound contains at least one radioactive halogen.

2. The compound of claim 1 wherein R is in the 4' position.

3. The compound of claim 2 wherein X is in the 10 position.

4. The compound of claim 3 wherein Y is in the 2 or 3 position.

5. The compound of claim 4 wherein R is selected from the group consisting of $^{123}$I, $^{124}$I, $^{125}$I, and $^{131}$I.

6. The compound of claim 5 wherein X is H and Y is H.

7. The compound of claim 5 wherein X is $^{18}$F and Y is H.

8. The compound of claim 5 wherein X is CH$_3$ and Y is H.

9. The compound of claim 5 wherein X is selected from the group consisting of $^{123}$I, $^{124}$I, $^{125}$I, and $^{131}$I, and Y is H.

10. The compound of claim 5 wherein X is H and Y is CH$_2^{18}$F.

11. The compound of claim 5 wherein X is $^{18}$F, and Y is CH$_2^{18}$F.

12. The compound of claim 5 wherein Y is CH$_2^8$F.

13. The compound of claim 5 wherein X is CH$_3$ and Y is CH$_2^{18}$F.

14. The compound of claim 4 wherein R is SCH$_3$ and Y is CH$_2^{18}$F.

15. The compound of claim 14 wherein X is selected from the group consisting of $^{123}$I, $^{124}$I, $^{125}$I, and $^{131}$I; and Y is CH$_2^{18}$F.

16. The compound of claim 14 wherein X is H and Y is CH$_2^{18}$F.

17. The compound of claim 14 wherein X is $^{18}$F, and Y is CH$_2^{18}$F.

18. The compound of claim 14 wherein X is CH$_3$, and Y is CH$_2^{18}$F.

19. The compound of claim 4 wherein R is —CH=CH—CH$_2$—$^{18}$F.

20. The compound of claim 19 wherein X is selected from the group consisting of $^{123}$I, $^{125}$I, and $^{131}$I; and Y is H.

21. The compound of claim 19 wherein X is H and Y is H.

22. The compound of claim 19 wherein X is $^{18}$F and Y is H.

23. The compound of claim 19 wherein and Y is H.

24. The compound of claim 19 wherein X is CH$_3$ and Y is H.

25. A compound of the formula:

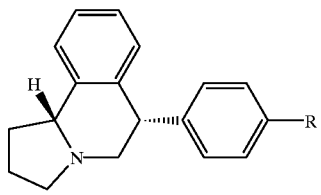

wherein R is selected from the group consisting of halogen, wherein said halogen is selected from the group consisting of $^{123}$I, $^{124}$I, $^{125}$I, $^{131}$I, $^{75}$Br, $^{76}$Br, $^{77}$Br, $^{82}$Br, $^{18}$F, and $^{210}$At; small alkyl, small alkenyl, or small alkynyl, any of which contains from one to about 6 carbon atoms and may have a carbon atom replaced by an O or S; or halogen substituted-small alkyl, halogen substituted-small alkenyl, or halogen substituted-small alkynyl wherein said compound contains at least one radioactive halogen.

26. The compound of claim 25 wherein R is a halogen.

27. The compound of claim 25 wherein R is selected from the group consisting of $^{123}$I, $^{124}$I, $^{125}$I, $^{131}$I, $^{75}$Br, $^{76}$Br, $^{77}$Br, $^{82}$Br, or —CH=CH—CH$_2$—X, wherein X is $^{18}$F.

28. The compound of claim 27 wherein R is $^{123}$I.

29. The compound of claim 27 wherein R is $^{82}$Br.

30. A kit for rapid synthesis of a radioactively labeled compound of claim 1 comprising (a) a compound having the structure:

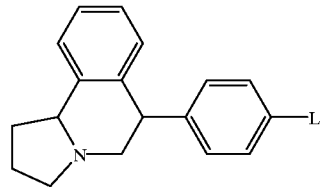

wherein L is a leaving group which is displaced by a radioactive group, and (b) a displacing reagent having a substituent containing a radioactive group wherein said radioactive group is $^{123}$I, $^{124}$I, $^{125}$I, $^{131}$I, $^{75}$Br, $^{76}$Br, $^{77}$Br, $^{82}$Br, or —CH=CH—CH$_2$—$^{18}$F.

31. A method for conducting positron emission tomography or single photon emission tomography imaging of a subject comprising administering to said subject an image-generating amount of a compound according to claim 1 and measuring the distribution within the subject of said compound by positron emission tomography or single photon emission tomography.

32. A method for conducting single photon emission imaging of a subject comprising administering to said subject an image-generating amount of a compound according to claim 1 and measuring the distribution within the subject of said compound by single photon emission tomography.

33. A method according to claim 32 wherein the compound of claim 1 contains at least one of the following: $^{75}$Br, $^{77}$Br, $^{123}$I or $^{131}$I, and measuring the distribution within the subject of said compound by single photon emission tomography.

34. The method of claim 31 wherein the halogen is selected from the group $^{76}$Br $^{75}$Br or $^{18}$F and the distribution of the compound is measured by positron emission tomography.

35. The method of claim 32 wherein the halogen is selected from the group $^{75}$Br, $^{75}$Br or $^{18}$F and the distribution of the compound is measured by single photon emission tomography.

* * * * *

UNITED STATES PATENT AND TRADEMARK OFFICE
CERTIFICATE OF CORRECTION

PATENT NO. : 6,162,417
DATED : December 19, 2000
INVENTOR(S) : Mark M. Goodman and Bing Z. Shi It is certified that error appears in the above-identified patent and that said Letters Patent is hereby corrected as shown below:

Title page,
First column, under "PUBLICATIONS", please delete "S-[78F]Fluoroethyl" and replace with -- S-[$^{18}$F]Fluoroethyl --.
Under "References Cited", please add

-- U.S. PATENT DOCUMENTS

| | | | |
|---|---|---|---|
| 4,908,450 | 3/13/90 | Maryanoff, B.E. et al | 546/94 |
| 4,837,328 | 6/6/89 | Maryanoff, B.E. et al | 546/94 |
| 4,719,216 | 1/12/88 | Maryanoff, B.E. et al | 514/292 |
| 4,713,386 | 12/15/87 | Maryanoff, B.E. et al | 514/294 |
| 4,595,688 | 6/17/86 | Maryanoff, B.E. et al | 514/285 |
| 4,572,911 | 2/25/86 | Carson J.R. et al | 514/291 |

OTHER PUBLICATIONS

Maryanoff, B.E. et al (1987) "Pyrroloisoquinoline antidepressants. In-depth exploration of structure-activity relationships" *J. Med Chem.* 30:1433-1454.
Suehiro, et al. (1992) "Synthesis of radiotracer for studying serotonin uptake sites with positron. emission tomography: [$^{11}$C]McN-5652-Z" *J. Label Cmpd. Radiopharm* 31:841-848.
Suehiro et al. (1993) "A PET radiotracer for studying serotonin uptake sites: carbon-11-McN-5652Z" *J. Nucl. Med.* 34:120-127. --

Column 10,
Line 61, please insert

-- than is seen. 3) The compound crosses the blood-brain barrier and thus the compound is available as a drug in the brain.

Further provided by this invention is a kit for the rapid synthesis of the compounds of Formula I. The kit includes a compound of Formula IV capable of reacting with a reagent capable of displacing L and replacing L with a substituent containing a radioactive group.

UNITED STATES PATENT AND TRADEMARK OFFICE
CERTIFICATE OF CORRECTION

PATENT NO. : 6,162,417
DATED : December 19, 2000
INVENTOR(S) : Mark M. Goodman and Bing Z. Shi It is certified that error appears in the above-identified patent and that said Letters Patent is hereby corrected as shown below:

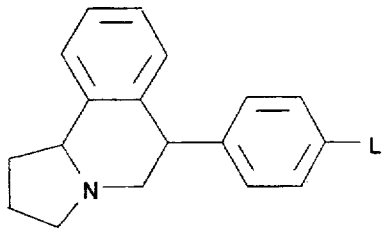

(IV)

L is a leaving group, as understood by those of ordinary skill in the art, and can be displaced by a positively charged halogen or substituent containing a positvely charged halogen. The compounds made by this kit can be used for diagnostics and imaging and hence preferably contain a radioactive isotope of a halogen. Preferably L is a metal, e.g., Sn, Hg, B, Si, and Ge.

The longer-lived isotopes, such as $^{123}$I with a half-life of 13 hours, are commercially available from sources such as Nordion International Ltd. (Vancouver, B. C., Canada) or NEN/DuPont (N.Billerica, MA). Shorter-lived isotopes, such as $^{18}$F can be obtained from a regional source, with a ~200 mile radius of the site of intended use.

The described kit is intended for use with a reagent capable of displacing L and replacing L with a substituent containing a radioactive group. For example, as will be understood by those in -- between "thyroid" and "the art,".

Column 12,
Line 43, please replace "y-aminoester" with -- γ-aminoester --.

Column 14,
Line 53, please change "2.893.03" with -- 2,89-3.03 --.

Column 16,
Line 25, please change "OCH$^2$" with -- OCH$_2$ --.

UNITED STATES PATENT AND TRADEMARK OFFICE
CERTIFICATE OF CORRECTION

PATENT NO.   : 6,162,417
DATED        : December 19, 2000
INVENTOR(S)  : Mark M. Goodman and Bing Z. Shi It is certified that error appears in the above-identified patent and that said Letters Patent is hereby corrected as shown below:

Column 19, claim 12,
Line 13, please change "$CH_2^8F$" with -- $CH_2^{18}F$ --.

Signed and Sealed this

Eighteenth Day of December, 2001

Attest:

Attesting Officer

JAMES E. ROGAN
Director of the United States Patent and Trademark Office